United States Patent [19]

Aikawa et al.

[11] 4,444,977

[45] Apr. 24, 1984

[54] CURABLE OXIRANE FORMULATIONS

[75] Inventors: Kiyoshi I. Aikawa, Matsudo, Japan; Ritchie A. Wessling, Midland, Mich.

[73] Assignee: The Dow Chemical Company, Midland, Mich.

[21] Appl. No.: 472,695

[22] Filed: Mar. 7, 1983

[51] Int. Cl.$^3$ ...................... C08G 59/62; C08G 59/40; C08G 59/42
[52] U.S. Cl. ..................................... 528/109; 523/414; 528/90; 528/361; 528/364
[58] Field of Search .................. 528/90, 109, 361, 364

[56] References Cited

U.S. PATENT DOCUMENTS

| | | | |
|---|---|---|---|
| 3,144,438 | 8/1964 | Sosnovsky | 260/329 |
| 3,544,499 | 12/1970 | Hatch | 260/29.6 |
| 3,793,278 | 2/1974 | De Bona | 260/29.2 EP |
| 4,020,030 | 4/1977 | Harris et al. | 260/29.2 EP |
| 4,331,574 | 5/1982 | Bekooij et al. | 525/530 |
| 4,337,185 | 6/1982 | Wessling et al. | 524/458 |

Primary Examiner—Earl A. Nielsen

[57] ABSTRACT

This invention is an aqueous-dispersible oxirane formulation comprising an oxirane and a cross-linking amount of 3-hydroxythiophane and an organic acid having at least 2 acid moieties that have a dissociation constant, $pK_a$, less than 4.75.

8 Claims, No Drawings

CURABLE OXIRANE FORMULATIONS

BACKGROUND OF THE INVENTION

This invention relates to curable oxirane formulations and methods for curing oxiranes to produce water-insoluble materials.

Most coating and other product formulations are employed in a fluidized state and are then dried or cured to solid continuous films or articles that are water-resistant. The films are also adherent to the substrate to which they are applied. Thus such fluid formulations usually contain a vehicle and miscellaneous ingredients such as pigments, extenders, fungicides and the like. The vehicle is a fluid consisting of a solution or a mixture of a binder with a thinner or solvent. The binder is the primary constituent since it binds itself and any optional ingredients to the substrate or surface of the object being coated. See, for example, Bobalek and Fisher, *Organic Protective Coatings*, Reinhold, (1953); and Martens, *Emulsion and Water-Soluble Paints and Coatings*, Reinhold (1964).

Of particular interest as coatings or binders are oxirane compounds such as epoxy resins and various polymers containing oxirane groups. To enable the coatings to dry or cure to form continuous adhesive films, the oxiranes that are cured after application to the substrate have generally been employed. In order that the coatings have a desired water resistance, the oxiranes used are generally hydrophobic and are therefore, not soluble in water. Thus, the liquid thinner or solvent, usually required to fluidize the oxiranes, has generally been an organic solvent such as xylene, toluene, various alcohols and the like. Such solvents are generally more expensive than water and are often toxic or flammable, thus requiring expensive precautions when coating formulations containing them are stored and used.

In view of the foregoing disadvantages of such organic solvents or thinners, it is highly desirable to employ an oxirane which can be dissolved by or dispersed in water and yet will produce a water-resistant film when applied to a substrate and then dried or cured. While such water-based fomulations have been made and cured in the past, it is desirable to provide curable oxirane formulations which cure to form coatings exhibiting further improvements in properties such as adhesion and water-resistance. It is also desirable that such formulations do not yield odorous by-products upon curing.

SUMMARY OF THE INVENTION

The present invention is such an aqueous-dispersible oxirane formulation comprising the reaction product of an oxirane and a cross-linking amount of 3-hydroxythiophane and an organic acid having at least 2 acid moieties that have a dissociation constant, $pK_a$, less than 4.75.

For purposes of this invention, an aqueous dispersible formulation means that (1) the formulation spontaneously forms a thermodynamically stable mixture with an aqueous medium including true solutions wherein individual molecules of the compound are dispersed as well as colloidal (micellular) solutions wherein the molecules are aggregated to some extent, or (2) the formulation can be dispersed in an aqueous medium without the aid of a surfactant to form a synthetic latex which is meta-stable in the thermodynamic sense. By an aqueous medium is meant water or a solution of a water-miscible polar liquid such as an alcohol or a cyclic ether in water.

In another aspect, this invention is a method for curing an oxirane which method comprises subjecting the oxirane formulations to conditions sufficient to form a sulfonium salt and then drying and heating the salt to cure the salt to a water-insoluble solid.

Surprisingly, the oxirane formulations of the present invention cure on exposure to heat to form highly water-resistant coatings or other materials having excellent physical properties such as adhesion, abrasion resistance and color without evolving observable amounts of undesirable sulfide odors. These formulations are usefully employed such as in paints, lacquers, paper coatings and flooring materials; as well as the binder components of adhesives, fiber-reinforced plastics and encapsulants.

DETAILED DESCRIPTION OF PREFERRED EMBODIMENTS

Oxiranes that are suitable for the purposes of this invention are polymeric compounds having more than one oxirane moiety per molecule and a minimum weight average molecular weight ($M_w$) of 300. Examples of such oxiranes are epoxy resins that bear more than 1, and preferably a plurality of pendant or terminal oxirane moieties (often called vicinal epoxy groups) such as the diglycidyl ether of bisphenol A and other polyglycidyl ethers of various polyols as well as the polyglycidyl esters of various polycarboxylic acids; polymers of glycidyl acrylates, methacrylates, haloacrylates and halomethacrylates; styryl oxiranes, styryl glycidyl ethers, and allylglycidyl ethers; and other resinous epoxy-containing reactants as described in U.S. Pat. No. 4,020,030. Of the foregoing oxiranes, the epoxy resins are preferred, with those having an average of 2 to 4 oxirane moieties per molecule such as described in U.S. Pat. No. 4,020,030 being especially preferred.

The 3-hydroxythiophene employed in this invention is a known compound which is readily prepared by the method set forth hereinafter in the Example.

Organic acids suitably employed in the practice of this invention are those acids having an organic moiety of at least 1 carbon and at least one acid moiety having a $pK_a$ of less than 4.75, preferably a carboxylic moiety having a $pK_a$ of less than 4.75, most preferably a $pK_a$ in the range from about 1 to about 4. Examples of such organic acids include the following acids and anhydrides: trimesic, terephthalic, isophthalic, phthalic, trimelletic, pyromelletic, formic, maleic and hydroxyacetic. Mono acids are preferred wherein the oxirane is to be rendered hydrophobic, but not substantially cross-linked by curing. Usually, in such cases, the oxirane is a polymer having sufficient molecular weight, e.g., $M_w$ greater than 10,000, preferably greater than 50,000, to yield a solid material having suitable strength and other properties desirable for coatings. Poly acids are preferred when the cured product is substantially cross-linked and the oxirane has a low molecular weight, e.g., $M_w$ less than 10,000, preferably a $M_w$ of 300–3000, as required for the manufacture of fiber-reinforced composities. Of these acids, trimesic and pyromelletic are preferred, with trimesic being especially preferred.

In the oxirane formulation, the oxirane is employed in an amount sufficient to provide structural integrity to the resultant cured article, e.g., film, coating, molded part, etc. The 3-hydroxythiophane and organic acid are employed in amounts sufficient to provide the desired cross-linking of the oxirane. Preferred oxirane formulations contain on an equivalent basis an excess of oxirane and acid to the 3-hydroxythiophane, preferably an equivalent ratio of

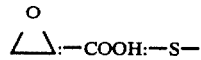

of 1.1:1.1:1 in order to minimize sulfide odor. Suitably, however, the components of the formulation may be employed on a 1:1:1 equivalent basis.

In the practice of the present invention, the oxirane formulation is preferably prepared by contacting an aqueous mixture of the organic acid and hydroxythiophane with the oxirane under conditions such that a sulfonium salt is formed as a result of the reaction between the oxirane moieties of the oxirane and the sulfide moiety of the 3-hydroxythiophane with the organic acid providing the anion of the resulting salt. In general, this salt is formed by heating the reaction mixture with stirring to a temperature from about 25° C. to about 100° C., preferably from about 50° C. to about 80° C.

The oxirane formulations are normally applied as an aqueous solution or an aqueous dispersion, e.g., a latex, thereof to the substrate and subsequently thermally cured or in some instances cured via radiation and heat. Convenient cure rates have been observed at temperatures of from about 60° C. to about 180° C., but higher or lower temperatures could be used at the convenience of the user. Normally such curing occurs at a temperature above the second order transition temperature ($T_g$) of the oxirane formulation. Alternatively, the oxirane formulation can be partially cured (B-stage) to a glassy state after removal of water and subsequently cured to completion by heating the partially cured polymer to a temperature above the $T_g$ of the fully cured product.

While these oxirane formulations can be employed as the sole binder in coating compositions, it is sometimes desirable to use them in combination with water-compatible, thermally-curable resins. Thus more extensive cross-linking may be achieved. Bronsted acids also catalyze this cross-linking reaction. Suitable water-compatible, thermally-curable resins include urea/formaldehyde resins, imino urea/formaldehyde resins, melamine/formaldehyde resins, phenol/formaldehyde resins and the like. Such resins are normally used in amounts of from about 5 to about 50 weight percent based on the weight of the oxirane formulation, and are preferably used in amounts from about 10 to about 30 weight percent. Alteratively, such additional resins may be blocked isocyanates containing tin catalysts as taught in EPO Application No. 14851 published Sept. 3, 1980. Other cross-linking agents can also be used in addition to or as substitutes for such water-compatible, thermally-curable resins. Other conventional additives can likewise be included in the instant coating compositions, such as leveling agents, pigments, fillers, cosolvents, foam control agents, etc.

The following examples are set forth to illustrate the invention and should not be construed as limiting its scope. Unless otherwise indicated all parts and percentages are by weight.

EXAMPLE 1

A. Preparation of 3-Hydroxythiophane

Into a two-liter reaction vessel containing 500 ml of a suspension of finely divided aluminum chloride (1.05 moles) in methylene chloride which is maintained between −10° C. and −20° C. is added 1 mole of chloroacetylchloride. Dry ethylene is then passed through the resulting solution while stirring and maintaining the temperature below 10° C. Absorption of the ethylene is rapid and ceases when a stoichiometric amount has been absorbed in approximately 3 hours under normal pressure. While continuing to maintain the temperature of the reaction mixture below 5° C., 110 ml of water is introduced dropwise into the reaction mixture thereby generating hydrogen chloride which is passed over 5 N NaOH solution. The reaction mixture is stirred vigorously for an additional hour after strong hydrogen chloride evolution has terminated. The reaction mixture is then filtered and the organic layer is withdrawn and vacuum distilled to provide an 80 percent yield of 1,4-dichloro-2-butanone.

One mole of the aforementioned butanone in 100 ml of methanol is contacted with 0.25 mole of aqueous sodium borohydride. The resulting mixture is extracted with methylene chloride and vacuum distilled to provide an 84 percent yield of 1,4-dichloro-2-butanol. This resulting 1,4-dichloro-2-butanol (1 mole) is added slowly over a period of 90 minutes to 586.2 g of an aqueous solution containing 1.1 moles of Na$_2$S.9H$_2$O at 70° C. under vigorous agitation. After the addition is complete, the mixture is held for an additional 60 minutes at 70° C., and a major portion of the methanol is removed by distillation. The resulting product is extracted with three 80-ml portions of methylene chloride and then vacuum distilled to provide 3-hydroxythiophane.

B. Preparation of Oxirane Formulation

A 10.4-g portion (0.1 mole) of 3-hydroxythiophane is introduced with stirring into a mixture of 7 g (0.033 mole) of trimesic acid and 10 g of water. The resulting mixture is then heated to 60° C. and 17.5 g (0.05 mole) of the diglydicyl ether of bisphenol A is introduced with vigorous stirring into the mixture. An immediate exothermic reaction is observed and the mixture becomes clear within 15–20 minutes. An additional 5 g of water is introduced with stirring, and the mixture is stirred thoroughly for an additional hour while maintaining the temperature of the mixture at 75° C. The resulting oxirane formulation which is a sulfonium salt represented by the structural formula:

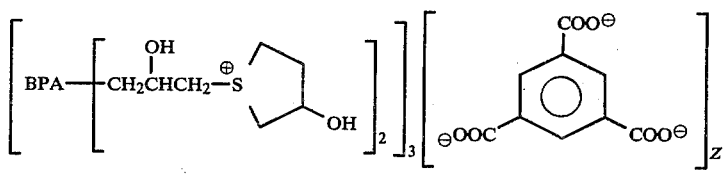

wherein BPA is represented by

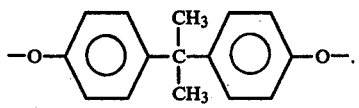

The clear mixture containing the aforementioned salt and 30 percent water is applied as a coating onto an aluminum panel and cured by heating to 150° C. for 5 minutes. No sulfide odor is detected during the cure. The coated panel is placed in boiling water for 30 minutes and exhibits no blushing or delamination.

What is claimed is:

1. An oxirane formulation comprising the reaction product of an oxirane and a cross-linking amount of 3-hydroxythiophane and an organic acid having at least 2 acid moieties that have a dissociation constant, $pK_a$, less than 4.75.

2. The formulation of claim 1 wherein the oxirane is an epoxy resin having more than one oxirane moiety per molecule and a minimum molecular weight ($M_w$) of 300.

3. The formulation of claim 1 wherein the acid is a carboxylic acid.

4. The formulation of claim 3 wherein the acid has one carboxylic acid moiety having a $pK_a$ in the range from about 1 to about 4.

5. The formulation of claim 1 wherein the acid is trimesic, terephthalic, phthalic, isophthalic, trimelletic, pyromelletic, formic, maleic and hydroxyacetic.

6. The formulation of claim 1 wherein the acid is trimesic.

7. A process for curing the formulation of claim 1 which comprises subjecting the formulation to conditions sufficient to form a sulfonium salt and then heating the salt to dryness to cure the salt to a water-insoluble solid.

8. The formulation of claim 1 wherein the oxirane and acid are employed in an excess to the 3-hydroxythiophane on an equivalent basis.